US012690959B2

(12) United States Patent
Pettlon, Sr. et al.

(10) Patent No.: US 12,690,959 B2
(45) Date of Patent: *Jul. 28, 2026

(54) ARTIFICIAL BLADDER SYSTEM

(71) Applicants: Ken Pettlon, Sr., Maryville, MO (US);
Kristopher Pettlon, Maryville, MO
(US)

(72) Inventors: Ken Pettlon, Sr., Maryville, MO (US);
Kristopher Pettlon, Maryville, MO
(US)

(73) Assignee: Ken Pettlon, Sr., Maryville, MO (US)

( * ) Notice: Subject to any disclaimer, the term of this
patent is extended or adjusted under 35
U.S.C. 154(b) by 860 days.

This patent is subject to a terminal dis-
claimer.

(21) Appl. No.: 18/046,208

(22) Filed: Oct. 13, 2022

(65) Prior Publication Data

US 2023/0056776 A1     Feb. 23, 2023

Related U.S. Application Data

(63) Continuation of application No. 17/546,111, filed on
Dec. 9, 2021, now Pat. No. 11,510,773, which is a
continuation of application No. 17/201,160, filed on
Mar. 15, 2021, now Pat. No. 11,202,700.

(51) Int. Cl.
*A61F 2/04*        (2013.01)
*A61F 2/48*        (2006.01)

(52) U.S. Cl.
CPC .............. *A61F 2/042* (2013.01); *A61F 2/482*
(2021.08); *A61F 2250/008* (2013.01)

(58) Field of Classification Search
CPC ........ A61F 2/042; A61F 2/7843; A61F 2/482;
A61F 2250/008; A61F 2/04; A61F
2005/0188
See application file for complete search history.

(56) References Cited

U.S. PATENT DOCUMENTS

| | | | |
|---|---|---|---|
| 6,296,668 B1 * | 10/2001 | Desgrandchamps ... | A61F 2/042 |
| | | | 623/23.65 |
| 2018/0028301 A1 * | 2/2018 | Sultan ...................... | A61B 5/03 |
| 2019/0091003 A1 * | 3/2019 | Forsell .................. | A61F 2/0036 |
| 2019/0388212 A1 * | 12/2019 | Ha .......................... | A61L 27/48 |

* cited by examiner

*Primary Examiner* — Sarah W Aleman
*Assistant Examiner* — Paris Marie Blass
(74) *Attorney, Agent, or Firm* — HOVEY WILLIAMS
LLP

(57) ABSTRACT

An artificial bladder system including an implantable blad-
der, a valve, a number of sensors, and an alert mechanism.
The implantable bladder includes an outer wall forming a
chamber for collecting urine of a user, the outer wall
including inflow openings and an outflow opening. The
valve is integrated with the outflow opening to selectively
allow urine to flow from the chamber through the outflow
opening. The sensors are configured to detect a urine level
in the chamber. The alert mechanism is configured to
generate a sensory output to alert the user that the bladder
should be emptied upon detection of the urine level in the
chamber by one of the sensors.

20 Claims, 3 Drawing Sheets

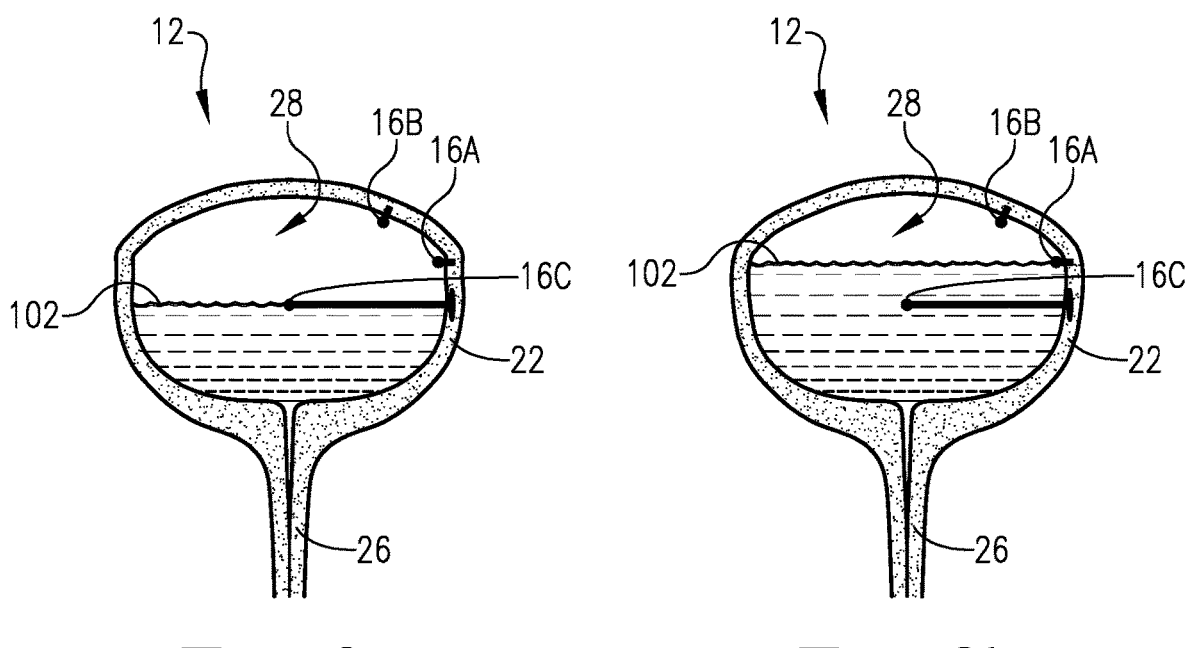
FIG. 2a                    FIG. 2b
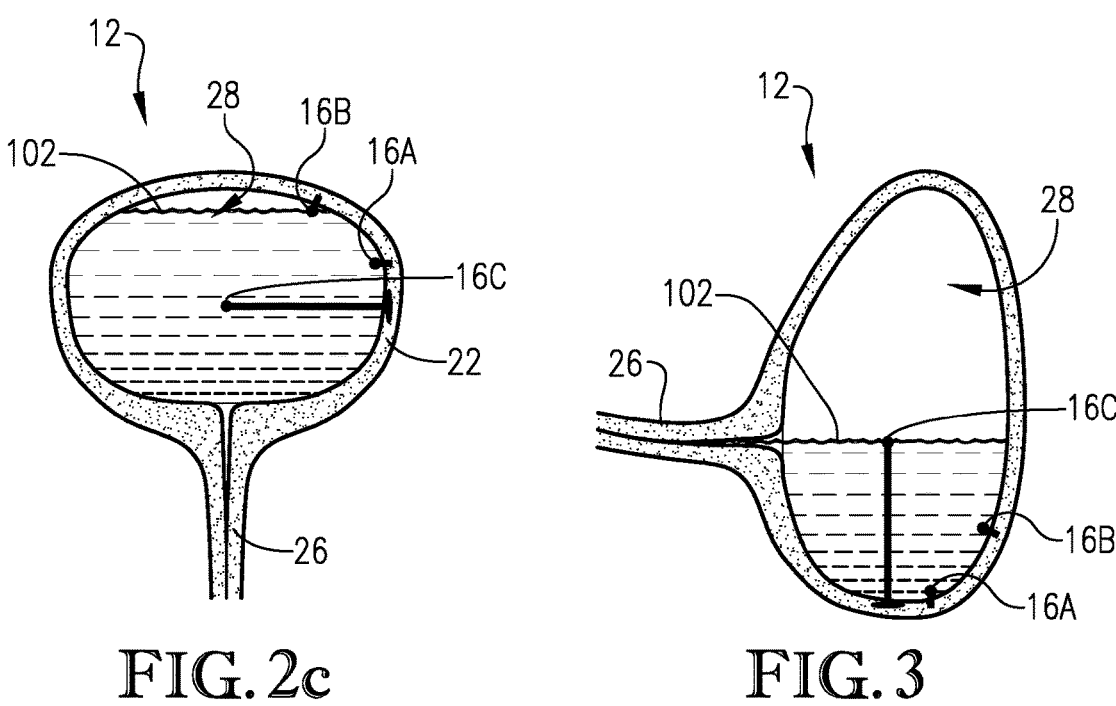
FIG. 2c                    FIG. 3

ARTIFICIAL BLADDER SYSTEM

RELATED APPLICATIONS

This patent application is a continuation application, and claims priority benefit with regard to all common subject matter, of earlier-filed U.S. patent application Ser. No. 17/546,111, filed on Dec. 9, 2021, and entitled "ARTIFICIAL BLADDER SYSTEM". Application Ser. No. 17/546,111 is a continuation application, and claims priority benefit with regard to all common subject matter, of earlier-filed U.S. patent application Ser. No. 17/201,160, filed on Mar. 15, 2021, and entitled "ARTIFICIAL BLADDER SYSTEM". The identified earlier-filed patent applications are hereby incorporated by reference in their entireties into the present application.

BACKGROUND

Victims/survivors of bladder cancer, prostate cancer, and other ailments often cannot use their bladders or may have their bladders removed. Such victims/survivors rely on external urine bags to collect urine. Urine bags are unwieldy and inconvenient and can easily be damaged. Urine bags may also cause mental stress, embarrassment, and inconvenience to the user.

SUMMARY

Embodiments of the invention solve the above-mentioned problems and other problems and provide a distinct advancement in the art of artificial bladder systems. More particularly, the invention provides an artificial bladder system including an implantable bladder. In some embodiments, the implantable bladder is functional in any orientation via at least two bladder orientation modes.

An embodiment of the invention is an artificial bladder system broadly comprising a bladder, a valve, a number of sensors, an alert mechanism, and a control pack. The artificial bladder system may be used by victims/survivors of bladder cancer, prostate cancer, and other ailments.

The bladder includes an outer wall, a number of inflow tubes, and an outflow tube. The bladder may be formed of latex, vinyl, surgical plastic, or any other suitable material.

The outer wall forms a chamber for collecting and storing urine. The outer wall may be sufficiently thick and stiff to be inserted into the user's abdomen in place of a natural bladder. The outer wall may house the valve, sensor wires, power wires, and other components.

The inflow tubes extend upward from upper portions of the bladder when the user and hence the bladder is in an upright orientation. The inflow tubes connect to the user's ureters.

The outflow tube extends downward from a bottom of the bladder when the user and hence the bladder is in the upright orientation. The outflow tube connects to the user's urethra.

The valve is positioned below the chamber in intricate flow communication with the outflow tube. The valve may also be embedded in the outer wall of the bladder or positioned in the chamber. The valve may be a plunger valve or any other suitable valve. In one embodiment, the valve includes a spring or similar biasing element for biasing the valve toward an open or closed position. The valve may also be hinged for allowing a catheter access to the chamber. The valve may also be weighted so that gravity biases the valve toward a closed position.

The sensors are positioned in various locations in the chamber for sensing urine levels in the chamber. A first sensor may be positioned near the outer wall to detect a first urine level. In one embodiment, first sensor is positioned to detect approximately sixty percent urine level when the bladder is in the upright orientation. A second sensor may be positioned near the outer wall above the first sensor to detect a second urine level greater than the first urine level. In one embodiment, the second sensor is positioned to detect approximately ninety percent urine level. A third sensor is positioned near a geometric center of the chamber to detect a third urine level regardless of the orientation of the bladder.

The alert mechanism is configured to generate a sensory output detectable by the user to alert the user that the bladder should be emptied, or for other indications. The alert mechanism may be configured to be positioned on or attached to the inside of the user's abdomen, or any other suitable location. The alert mechanism may be a vibrator, a light emitter, or other device.

The control pack includes a toggle switch, a number of buttons, a battery, a connector, and a controller. The control pack may be configured to be positioned outside of and adjacent to or near the user's body. For example, the control pack may be held against the user's body via a strap or similar mechanism. Alternatively, the control pack may be clipped to the user's garments, placed in a pocket of the user's garments, handheld, or the like. The control pack may be waterproof or water resistant. The control pack may also be a user's mobile device, pager, remote control, or the like. The artificial bladder system may include an extra control pack in case the control pack does not work as intended, runs out of battery power, or cannot be found.

The toggle switch allows the user to switch between upright mode and prone mode. Alternatively, a button, knob, touch interface, voice command system or the like may be used.

The buttons allow the user to cause the controller to open and close the valve. Alternatively, a toggle switch, knob, touch interface, voice command system, or the like may be used.

The battery provides power to the valve, the sensors, the alert mechanism, and the controller. The battery may be a mobile phone style battery or any other suitable battery. The battery may be rechargeable, disposable, or replaceable.

The connector electronically links the control pack to the valve, the sensors, and the alert mechanism. The connector may be positioned near an outside of the user's abdomen so that when the connector is detached, minimal wiring is exposed from the user. Alternatively, the control pack may be configured to wirelessly communicate with the valve, sensors, and alert mechanism.

The controller provides control for the artificial bladder system and may be or may include a processor, circuit board, memory, and other electronic circuit elements such as resistors, capacitors, transistors, and the like. The controller is in wired communication with the valve, the sensors, and the alert mechanism via the connector. Alternatively, the controller may be in wireless communication with these components.

The wires described above (connecting the various components of the artificial bladder system) may be encased or enclosed in a plastic tube or similar element. Portions of the wires may also be embedded in the outer wall of the bladder.

In use, the artificial bladder system may be operated in an upright mode and a prone mode. To switch between these modes, the user may flip the switch on the control pack. Alternatively, the artificial bladder system may detect an orientation of the user, and hence the bladder and automatically switch between these modes.

In the upright mode, the artificial bladder system operates with the bladder in an upright orientation such as when the user is sitting, standing, or walking. The first sensor detects a first urine level, such as approximately sixty percent. The controller then receives a signal from the first sensor that the first urine level has been detected, indicating the bladder should be emptied. The controller then generates a signal and sends this signal to the alert mechanism to activate the alert mechanism. The alert mechanism then generates a sensory output to alert the user that the bladder should be emptied. The sensory output may continue for a certain amount of time, such as ten seconds. The alert mechanism may generate another sensory output after a certain time has lapsed, such as every sixty seconds, if the valve has not been opened yet.

The user then presses one of the buttons on the control pack to cause the controller to generate another signal and send this signal to the valve to open. The valve then opens, thus allowing the bladder to empty. The valve then closes after a certain amount of time, such as thirty seconds, or after the bladder has emptied. Alternatively, the user may press another one of the buttons on the control pack to cause the controller to generate another signal and send this signal to the valve to close.

If the user has not emptied the bladder despite receiving the sensory output, or if an error in the artificial bladder system prevents the alert mechanism from generating the sensory output, the bladder may continue filling with urine. The second sensor may then detect a second urine level, such as approximately ninety percent. The controller then receives a signal from the second sensor that the second urine level has been detected, indicating the bladder is almost full. The controller then generates a signal and sends this signal to the valve to open. The valve then opens, thus allowing the bladder to empty. Note that this does not involve the user and thus allows the bladder to be emptied before excessive urine causes damage to the user or to the artificial bladder system.

In the prone mode, the artificial bladder system operates with the bladder in a prone orientation such as when the user is laying on his back, his left side, his right side, or his stomach, or even when the user is inverted. The prone mode also works when the user is upright. The third sensor detects a third urine level, such as approximately fifty percent. The controller then receives a signal from the third sensor that the third urine level has been detected, indicating the bladder should be emptied. The controller then generates a signal and sends this signal to the alert mechanism to activate the alert mechanism. The alert mechanism then generates a sensory output to alert the user that the bladder should be emptied. The sensory output may continue for a certain amount of time, such as ten seconds, or until the valve has been opened. The alert mechanism may generate another sensory output after a certain time has lapsed, such as every sixty seconds, if the valve has not been opened yet. The sensory outputs generated in the prone mode may be enhanced, heightened, or intensified to alert the user when the user is sleeping or resting. Alternatively, different sensory outputs (relative to the ones used in the upright mode) more suitable for waking a sleeping user may be employed. The controller may instruct the valve to open automatically after a certain time has lapsed, such as two minutes.

The user then presses one of the buttons on the control pack to cause the controller to generate another signal and send this signal to the valve to open. The valve then opens, thus allowing the bladder to empty. The valve may then close after a certain amount of time, such as thirty seconds, or after the bladder has emptied. Alternatively, the user may press another one of the buttons on the control pack to cause the controller to generate another signal and send this signal to the valve to close.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

BRIEF DESCRIPTION OF THE DRAWING FIGURES

Embodiments of the present invention are described in detail below with reference to the attached drawing figures, wherein:

FIG. 2a is a cutaway elevation view of an implantable bladder of the artificial bladder system of FIG. 1 in an upright orientation;

FIG. 2b is a cutaway elevation view of the implantable bladder of FIG. 2a;

FIG. 2c is a cutaway elevation view of the implantable bladder of FIG. 2a;

FIG. 3 is a cutaway elevation view of the implantable bladder of FIG. 2a in a prone orientation;

Figure 1:
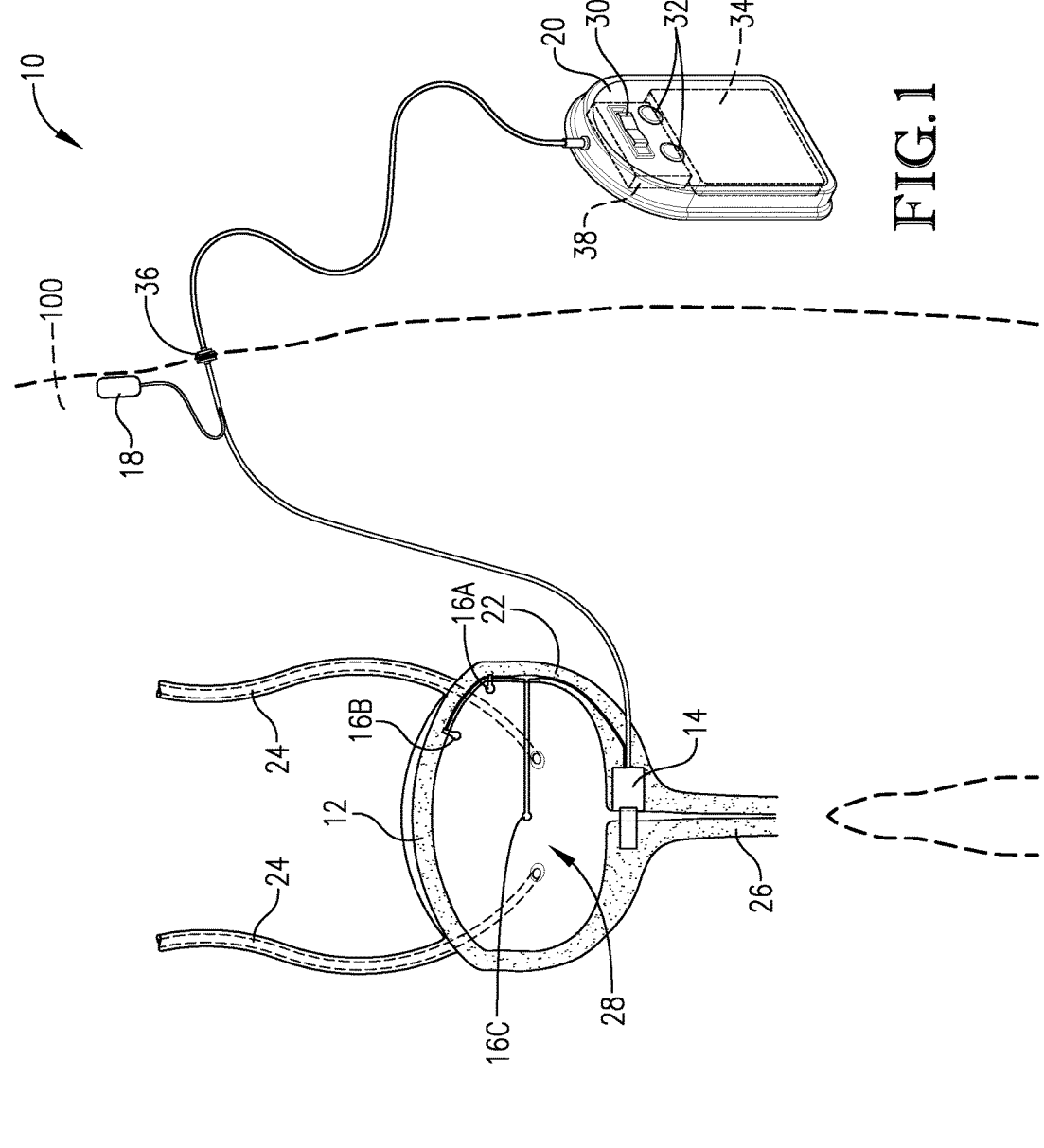
FIG. 1 is a partial cutaway elevation view of an artificial bladder system constructed in accordance with an embodiment of the invention.
Figure 4:
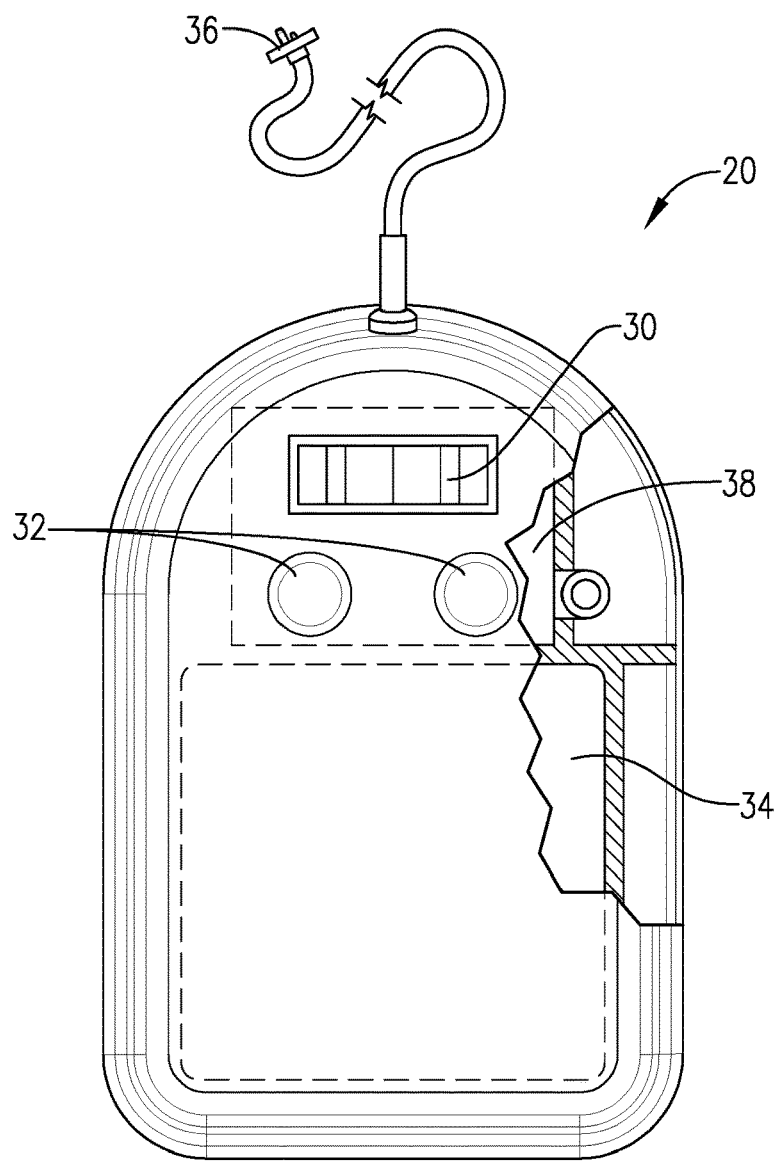
FIG. 4 is a partial cutaway elevation view of a control pack of the artificial bladder system of FIG. 1.
Figure 5:
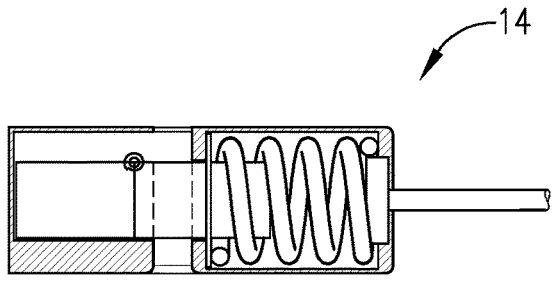
FIG. 5 is a cutaway elevation view of a valve of the artificial bladder system of FIG. 1.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein. Directional terms such as "longitudinal" and "lateral" are generally in reference to a standard aircraft orientation. For example, longitudinal features may be generally aligned with the aircraft's primary direction of travel while lateral features may extend horizontally perpendicular to the aircraft's primary direction of travel.

Turning to the drawing figures, an artificial bladder system 10 constructed in accordance with an embodiment of the invention is illustrated. The artificial bladder system 10 broadly comprises a bladder 12, a valve 14, a plurality of sensors 16A-C, an alert mechanism 18, and a control pack 20.

The bladder 12 may include an outer wall 22, a plurality of inflow tubes 24, and an outflow tube 26. The bladder 12 may be formed of latex, vinyl, surgical plastic, or any other suitable material.

The outer wall 22 forms a chamber 28 for collecting and storing urine. The outer wall 22 may be sufficiently thick and stiff to be inserted into the user's abdomen in place of a natural bladder. The outer wall 22 may house the valve 14, sensor wires, power wires, and other components.

The inflow tubes 24 may extend upward from upper portions of the bladder 12 when the user and hence the bladder 12 is in an upright orientation. The inflow tubes 24 may connect to the user's ureters and may be spaced from each other similar to natural ureter-bladder connections. In another embodiment, the bladder 12 connects directly to the user's ureters such that distinct inflow tubes 24 are not required. The inflow tubes 24 may be spaced from the plurality of sensors 16A-C so inflow of urine from the inflow tubes 24 does not interfere with sensor readings.

The outflow tube 26 may extend downward from a bottom of the bladder 12 when the user and hence the bladder 12 is in the upright orientation. The outflow tube 26 may connect to the user's urethra. In another embodiment, the bladder 12 connects directly to the user's urethra such that a distinct outflow tube 26 is not required. The outflow tube 26 is in intricate flow communication with the valve 14 so that the valve 14 dictates flow through the outflow tube 26.

The valve 14 may be positioned below the chamber 28 in intricate flow communication with the outflow tube 26. The valve 14 may also be embedded in the outer wall 22 of the bladder 12 or positioned in the chamber 28. The valve 14 may be a plunger valve or any other suitable valve. In one embodiment, the valve 14 includes a spring or similar biasing element for biasing the valve 14 toward an open or closed position. The valve 14 may also be hinged for allowing a catheter access to the chamber 28. The valve 14 may be weighted so that gravity biases the valve 14 toward the closed position. The valve 14 may be formed of surgical stainless steel or any other suitable material.

The plurality of sensors 16A-C may be positioned in various locations in the chamber 28 for sensing urine levels in the chamber 28, as best seen in FIGS. 2a-3. Sensor 16A may be positioned near the outer wall 22 to detect a first urine level. In one embodiment, sensor 16A is positioned to detect approximately sixty percent urine level when the bladder 12 is in the upright orientation. Sensor 16B may be positioned near the outer wall 22 above sensor 16A to detect a second urine level greater than the first urine level. In one embodiment, sensor 16B is positioned to detect approximately ninety percent urine level. Sensor 16C may be positioned near a geometric center of the chamber 28 to detect a third urine level regardless of the orientation of the bladder 12, as seen in FIGS. 2a and 3. That is, sensor 16C may be positioned to detect approximately fifty percent urine level when the bladder 12 is in a side orientation, a back (prone) orientation (FIG. 3), or a front orientation. Sensor 16C may also be positioned to detect approximately fifty percent urine level even when the bladder 12 is in the upright orientation (FIG. 2a), but sensor 16C may not be active/in use in this case as described in more detail below. The plurality of sensors 16A-C may be made of surgical stainless steel or other suitable material.

The alert mechanism 18 may be configured to generate a sensory output detectable by the user to alert the user that the bladder 12 should be emptied, or for other indications. The alert mechanism 18 may be configured to be positioned on or attached to the inside of the user's abdomen, or any other suitable location. The alert mechanism 18 may be a vibrator, a light emitter, or other device. The alert mechanism 18 may be configured to generate vibrations, a light signal, a nerve stimulation, or any other suitable sensory output.

The control pack 20 may include a toggle switch 30, a plurality of buttons 32, a battery 34, a connector 36, and a controller 38. The control pack 20 may be configured to be positioned outside of and adjacent to or near the user's body. For example, the control pack 20 may be held against the user's body via a strap or similar mechanism. Alternatively, the control pack 20 may be clipped to the user's garments, placed in a pocket of the user's garments, handheld, or the like. The control pack 20 may be waterproof or water resistant so that the user can take or wear the control pack 20 in a bathing environment or to continue working if rain, urine, or other liquid comes into contact with the control pack 20. The control pack 20 may also be a user's mobile device, pager, remote control, or the like. The artificial bladder system 10 may include an additional, backup, redundant, or secondary control pack in case the control pack 20 does not work as intended, runs out of battery power, or cannot be found.

The toggle switch 30 may allow the user to switch between upright mode and prone mode. Alternatively, a button, knob, touch interface, voice command system or the like may be used.

The plurality of buttons 32 allow the user to cause the controller 38 to open and close the valve 14. Alternatively, a toggle switch, knob, touch interface, voice command system, or the like may be used.

The battery 34 provides power to the valve 14, the sensors 16A-C, the alert mechanism 18, and/or the controller 38. The battery 34 may be a mobile phone style battery or any other suitable battery. The battery 34 may be rechargeable, disposable, or replaceable.

The connector 36 electronically links the control pack 20 to the valve 14, the plurality of sensors 16A-C, and the alert mechanism 18. The connector 36 may be positioned near an outside of the user's abdomen so that when the connector is detached, minimal wiring is exposed from the user. Alternatively, the control pack 20 may be configured to wirelessly communicate with the valve 14, plurality of sensors 16A-C, and alert mechanism 18. In this case, communication components such as an antenna or transceiver may be used. Wireless communication such as RF transmissions, Near Field Communications (NFC), Bluetooth® communication, or any other suitable wireless communication may be used.

The controller 38 provides control for the artificial bladder system 10 and may be or may include a processor, circuit board, memory, and other electronic circuit elements such as resistors, capacitors, transistors, and the like. The controller 38 is in wired communication with the valve 14, the plurality of sensors 16A-C, and the alert mechanism 18 via the connector 36. Alternatively, the controller 38 may be in wireless communication with these components.

The wires described above (connecting the various components of the artificial bladder system 10) may be encased or enclosed in a plastic tube or similar element. Portions of the wires may also be embedded in the outer wall 22 of the bladder 12.

In use, the artificial bladder system 10 may be operated in an upright mode and a prone mode. To switch between these modes, the user may flip the switch 30 on the control pack 20. Alternatively, the artificial bladder system 10 may detect an orientation of the user, and hence the bladder 12 and automatically switch between these modes.

In the upright mode, the artificial bladder system 10 operates with the bladder 12 in an upright orientation such as when the user is sitting, standing, or walking. Sensor 16A may detect a first urine level, such as approximately sixty percent. The controller 38 may then receive a signal from the sensor 16A that the first urine level has been detected, indicating the bladder 12 should be emptied. The controller 38 may then generate a signal and send this signal to the alert mechanism 18 to activate the alert mechanism 18. The alert mechanism 18 may then generate a sensory output to alert the user that the bladder 12 should be emptied. In one embodiment, vibrations may be generated, but other sensory outputs such as sounds for the feeling impaired, or lights for the hearing impaired, etc. may be employed. The sensory output may continue for a certain amount of time, such as ten seconds. The alert mechanism 18 may generate another sensory output after a certain time has lapsed, such as every sixty seconds, if the valve 14 has not been opened yet.

The user may then press one of the buttons 32 on the control pack 20 to cause the controller 38 to generate another signal and send this signal to the valve 14 to open. The valve 14 may then open, thus allowing the bladder 12 to empty. The valve 14 may then close after a certain amount of time, such as thirty seconds, or after the bladder 12 has emptied. Alternatively, the user may press another one of the buttons 32 on the control pack 20 to cause the controller 38 to generate another signal and send this signal to the valve 14 to close.

If the user has not emptied the bladder 12 despite receiving the sensory output, or if an error in the artificial bladder system 10 prevents the alert mechanism from generating the sensory output, the bladder 12 may continue filling with urine. Sensor 16B may then detect a second urine level, such as approximately ninety percent. The controller 38 may then receive a signal from the sensor 16B that the second urine level has been detected, indicating the bladder 12 is almost full. The controller 38 may then generate a signal and send this signal to the valve 14 to open. The valve 14 may then open, thus allowing the bladder 12 to empty. Note that this does not involve the user and thus allows the bladder 12 to be emptied before excessive urine causes damage to the user or to the artificial bladder system 10.

In the prone mode, the artificial bladder system 10 operates with the bladder 12 in a prone orientation such as when the user is laying on his back, his left side, his right side, or his stomach, or even when the user is inverted. The prone mode also works when the user is upright. Sensor 16C may detect a third urine level, such as approximately fifty percent. The controller 38 may then receive a signal from the sensor 16C that the third urine level has been detected, indicating the bladder 12 should be emptied. The controller

38 may then generate a signal and send this signal to the alert mechanism 18 to activate the alert mechanism 18. The alert mechanism 18 may then generate a sensory output to alert the user that the bladder 12 should be emptied. The sensory output may continue for a certain amount of time, such as ten seconds, or until the valve 14 has been opened. The alert mechanism 18 may generate another sensory output after a certain time has lapsed, such as every sixty seconds, if the valve 14 has not been opened yet. The sensory outputs generated in the prone mode may be enhanced, heightened, or intensified to alert the user when the user is sleeping or resting. Alternatively, different sensory outputs (relative to the ones used in the upright mode) more suitable for waking a sleeping user may be employed. The controller 38 may instruct the valve 14 to open automatically after a certain time has lapsed, such as two minutes.

The user may then press one of the buttons 32 on the control pack 20 to cause the controller 38 to generate another signal and send this signal to the valve 14 to open. The valve 14 may then open, thus allowing the bladder 12 to empty. The valve 14 may then close after a certain amount of time, such as thirty seconds, or after the bladder 12 has emptied. Alternatively, the user may press another one of the buttons 32 on the control pack 20 to cause the controller 38 to generate another signal and send this signal to the valve 14 to close.

The above-described artificial bladder system 10 provides several advantages. For example, the artificial bladder system 10 allows a user to have full bladder control with minimal external components and no external bladder or bag. The artificial bladder system 10 can operate in upright and prone modes, the latter of which can ensure an accurate urine level detection in any orientation due to the sensor 16C being positioned in the geometric center of the chamber 28. The valve 14 provides fail-open operation and allows use of a catheter in an emergency. The sensor 16B prevents the bladder 12 from becoming too full. The artificial bladder system 10 can be customized to the user's needs such as specific sensory outputs. The valve 14 and connecting valve and portions of sensor wires are protected in the outer wall 22 of the bladder 12.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An artificial bladder system comprising:

an implantable bladder including an outer wall forming a chamber for collecting urine of a user, the outer wall including inflow openings and an outflow opening;

a valve integrated with the outflow opening to selectively allow urine to flow from the chamber through the outflow opening; and a sensor configured to detect a urine level in the chamber, the sensor being positioned in the middle of the chamber to detect the urine level at approximately fifty percent in at least two different orientations of the bladder.

2. The artificial bladder system of claim 1, further comprising an alert mechanism configured to generate a sensory output to alert the user that the bladder should be emptied.

3. The artificial bladder system of claim 2, the alert mechanism being configured to be attached to an abdomen wall of the user.

4. The artificial bladder system of claim 1, further comprising an alert mechanism configured to generate a sensory output having a first characteristic due to the bladder being in a non-prone position and generate a sensory output having a second characteristic different than the first characteristic due to the bladder being in a prone position.

5. The artificial bladder system of claim 1, further comprising a battery configured to supply electrical power to the valve, the valve being configured to open when power is not provided to the valve or when the artificial bladder system has faulted.

6. The artificial bladder system of claim 1, the valve including a spring-loaded hinge shiftable to an open position via a catheter and automatically shiftable to a closed position upon removal of the catheter.

7. The artificial bladder system of claim 1, the valve being embedded in the outer wall of the bladder.

8. An artificial bladder system comprising:

an implantable bladder including an outer wall forming a chamber for collecting urine of a user, the outer wall including inflow openings and an outflow opening;

a valve integrated with the outflow opening to selectively allow urine to flow from the chamber through the outflow opening; and a plurality of sensors configured to detect a urine level in the chamber, the plurality of sensors including a sensor positioned in the middle of the chamber to detect the urine level at approximately fifty percent in at least two different orientations of the bladder.

9. The artificial bladder system of claim 8, further comprising an alert mechanism configured to generate a sensory output to alert the user that the bladder should be emptied.

10. The artificial bladder system of claim 9, the alert mechanism being configured to be attached to an abdomen wall of the user.

11. The artificial bladder system of claim 8, further comprising an alert mechanism configured to generate a sensory output having a first characteristic due to the bladder being in a non-prone position and generate a sensory output having a second characteristic different than the first characteristic due to the bladder being in a prone position.

12. The artificial bladder system of claim 8, further comprising a battery configured to supply electrical power to the valve, the valve being configured to open when power is not provided to the valve or when the artificial bladder system has faulted.

13. The artificial bladder system of claim 8, the valve including a spring-loaded hinge shiftable to an open position via a catheter and automatically shiftable to a closed position upon removal of the catheter.

14. The artificial bladder system of claim 8, the valve being embedded in the outer wall of the bladder.

15. An artificial bladder system comprising:

an implantable bladder including an outer wall forming a chamber for collecting urine of a user, the outer wall including inflow openings and an outflow opening;

a valve integrated with the outflow opening to selectively allow urine to flow from the chamber through the outflow opening; and a first sensor positioned near the outer wall to detect a first urine level;

a second sensor positioned near the outer wall above the first sensor to detect a second urine level greater than the first urine level; and a third sensor positioned in the middle of the chamber to detect a urine level at approximately fifty percent in at least two different orientations of the bladder.

16. The artificial bladder system of claim 15, further comprising an alert mechanism configured to generate a sensory output to alert the user that the bladder should be emptied.

17. The artificial bladder system of claim 16, the alert mechanism being configured to be attached to an abdomen wall of the user.

18. The artificial bladder system of claim 16, the alert mechanism being configured to generate an enhanced sensory output when the bladder is in a prone position.

19. The artificial bladder system of claim 15, further comprising a battery configured to supply electrical power to the valve, the valve being configured to open when power is not provided to the valve or when the artificial bladder system has faulted.

20. The artificial bladder system of claim 15, the valve including a spring-loaded hinge shiftable to an open position via a catheter and automatically shiftable to a closed position upon removal of the catheter.

* * * * *